(12) United States Patent
Liu

(10) Patent No.: US 8,383,701 B2
(45) Date of Patent: Feb. 26, 2013

(54) POLYMER ENCAPSULATED PIGMENT DISPERSION WITH HIGH SOLIDS CONTENT

(75) Inventor: Hui Liu, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1412 days.

(21) Appl. No.: 11/800,351

(22) Filed: May 4, 2007

(65) Prior Publication Data

US 2008/0275163 A1 Nov. 6, 2008

(51) Int. Cl.
*C08K 9/04* (2006.01)
*B01J 13/02* (2006.01)

(52) U.S. Cl. .... 523/205; 523/400; 523/160; 428/402.24

(58) Field of Classification Search .............. 428/402.24
See application file for complete search history.

(56) References Cited

U.S. PATENT DOCUMENTS

| | | | |
|---|---|---|---|
| 4,608,401 A * | 8/1986 | Martin | 523/205 |
| 4,680,200 A * | 7/1987 | Solc | 427/213.34 |
| 4,771,086 A | 9/1988 | Martin | |
| 5,234,711 A | 8/1993 | Kamen et al. | |
| 6,489,382 B1 * | 12/2002 | Giesecke et al. | 524/89 |
| 6,767,090 B2 | 7/2004 | Yatake et al. | |
| 6,972,303 B1 | 12/2005 | Miyabayashi et al. | |
| 2003/0144376 A1 | 7/2003 | Vincent et al. | |
| 2004/0229974 A1 | 11/2004 | Miyabayashi | |

FOREIGN PATENT DOCUMENTS

WO 2005105931 11/2005

OTHER PUBLICATIONS

Lelu et al., "Encapsulation of an organic phthalocyanine blue pigment into polystyrene latex particles using a miniemulsion polymerization process", Polymer International, 52:542-547, 2003.
Tiarks et al., "Encapsulation of Carbon Black by Miniemulsion Polymerization", Macromol. Chem. Phys. 2001, vol. 202, No. 1, 51-60.
European Search Report for Application No. 08746890.6-1214/ 2147065 PCT/US2008061558, Reference 200700810-4, Hewlet-Packard Development Company, L.P., Nov. 23, 2010.

* cited by examiner

*Primary Examiner* — James J Seidleck
*Assistant Examiner* — S. Camilla Pourbohloul

(57) ABSTRACT

The present invention is drawn to a method of forming an encapsulated pigment dispersion and pigment dispersions that can be prepared therefrom. The method includes mixing a pigment particle in liquid vehicle dispersion with a miniemulsion of monomers. A redox initiating agent is added to the liquid vehicle and the monomers are polymerized on the surface of the pigment particles. The resulting encapsulated pigment dispersion has a total solid content of at least 12 wt %.

16 Claims, No Drawings

POLYMER ENCAPSULATED PIGMENT DISPERSION WITH HIGH SOLIDS CONTENT

BACKGROUND OF THE INVENTION

The majority of inks and toners used in the printing industry employ water insoluble polymers for print adhesion and durability. Water-based inks, such as used in ink-jet printing, can incorporate water insoluble polymers as dispersed particulates. The particulates are typically designed to allow formation of a print-film on the printed substrate. Alternatively, these water insoluble polymers can be coated on the surface of pigments in the form of polymer-encapsulated pigments.

While some encapsulation methods and chemistries are known, dispersions including such polymer encapsulated pigments often don't exhibit stability in dispersions having relatively high solids content. Therefore, many encapsulation methods, e.g. those including potassium persulfate, are carried out with low solids content. Unfortunately, although dispersions with lower solids content exhibit improved stability, they are difficult, if not impossible, to utilize in such products as inks. As dispersions having low solids content, and thus low pigment content, are diluted by incorporation into an ink, the overall pigment content of the ink is likewise limited.

Thus, there is a continued need for development of stable polymer encapsulated pigment dispersions that have high solids content.

DETAILED DESCRIPTION OF THE PREFERRED EMBODIMENT(S)

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It is noted that, as used in this specification and the appended claims, the singular forms "a," "an," and "the" include plural referents unless the context clearly dictates otherwise.

As used herein, "liquid vehicle" refers to a liquid in which pigment particles are dispersed. Liquid vehicles are well known in the art, and a wide variety of liquid vehicles may be used in accordance with embodiments of the present invention. Such liquid vehicles may include a mixture of a variety of different agents, including without limitation, surfactants, solvents, co-solvents, buffers, biocides, viscosity modifiers, sequestering agents, stabilizing agents, and/or water.

As used herein, "ink vehicle" refers to a sub-class of liquid vehicle. Ink vehicle is the liquid fluid in which colorant in the form of encapsulated pigment is dispersed to form an ink. In some cases, in accordance with embodiments of the present invention, ink vehicles can include a mixture of a variety of different agents, such are listed with the definition of liquid vehicle.

As used herein, "plurality" refers to more than one. For example, a plurality of monomers refers to at least two monomers.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

The term "substantially free" refers to the total absence of or near total absence of a specific compound or composition. For example, when a composition is said to be substantially free of non-encapsulated pigment, there is either no non-encapsulated pigment in the composition or only trace amounts of non-encapsulated pigment in the composition. Likewise, the term "substantially" refers to the complete or nearly complete extent or degree of an action, characteristic, property, state, structure, item, or result. The exact allowable degree of deviation from absolute completeness may in some cases depend on the specific context. However, generally speaking the nearness of completion will be so as to have the same overall result as if absolute and total completion were obtained.

"Pigment" can include color-imparting particulates and other substances that may be suspended or solvated in a liquid vehicle with polymer-encapsulation in accordance with embodiments of the present invention. In one aspect, the pigment can be a dispersant-dispersed pigment that typically utilizes a dispersant (which can be a polymer, an oligomer or a surfactant) in the liquid vehicle to aid the pigment in becoming and/or substantially remaining dispersed in a liquid vehicle. With respect to the other particulates that can be used, examples include semi-metal and metal particulates, semi-metal oxide and metal oxide particulates, dispersible silicates and glass particulates, ferromagnetic and other magnetic particulates, whether or not such particulates impart color. In the present invention, the pigment particles are typically dispersed in a medium such as water.

As used herein, a plurality of items, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "0.1 wt % to 5 wt %" should be interpreted to include not only the explicitly recited concentration of 0.1 wt % to 5 wt %, but also include individual concentrations and the sub-ranges within the indicated range. Thus, included in this numerical range are individual concentrations, such as 1 wt %, 2 wt %, 3 wt %, and 4 wt %, and sub-ranges, such as from 0.1 wt % to 1.5 wt %, 1 wt % to 3 wt %, from 2 wt % to 4 wt %, from 3 wt % to 5 wt %, etc. This same principle applies to ranges reciting only one numerical value. For example, a range recited as "less than 5 wt %" should be interpreted to include all values and sub-ranges between 0 wt % and 5 wt %. Furthermore, such an interpretation should apply regardless of the breadth of the range or the characteristics being described.

With these definitions in mind, a method of forming an encapsulated pigment dispersion, comprising multiple steps, including forming a pigment dispersion by dispersing pigment particles in a liquid vehicle; and forming a mini-emulsion of monomers in an aqueous solution by a high energy dispersing method. Other steps include mixing the mini-emulsion with the pigment dispersion to produce a prepolymer mixture; adding a redox initiating agent to the prepolymer mixture; and polymerizing the monomers on a surface of the pigment particles to form the encapsulated pigment dispersion having a total encapsulated pigment solids content of at least 12 wt %. In another embodiment, a method of forming an ink-jet ink can comprise preparing the encapsulated pigment dispersion described above, and mixing the encapsulated pigment dispersion in an aqueous ink vehicle.

In another embodiment, an encapsulated pigment dispersion can comprise a liquid vehicle and a plurality of polymer encapsulated pigment particles dispersed in the liquid vehicle. The encapsulated pigment dispersion can have a total encapsulated pigment solids content of about 18 wt % to about 40 wt %, or from 25 wt % to 40 wt %. The encapsulated pigment dispersion can alternatively have a total encapsulated pigment solids content of about 25 wt % to about 40 wt %. Optionally, the dispersed polymer encapsulated pigment particles can have a polymer capsule to pigment weight ratio of at least about 1:1.

In accordance with the difficulties outlined, various details are provided herein which are applicable to each of the encapsulated pigment dispersion, ink-jet ink, and methods for making the dispersion and ink-jet ink. Thus, discussion of one specific embodiment is related to and provides support for this discussion in the context of the other related embodiments.

Regarding the individual steps, the method can include dispersing pigment particles in a liquid vehicle. Such pigment dispersions can be pre-dispersed or ready-made so as to be purchased as pigment particles dispersed in a liquid vehicle. In such cases, it may or may not be desirable to add additional liquid vehicle to the dispersion. Therefore, dispersing pigment particles in a liquid vehicle can, in some cases, include purchasing and using a dispersion that includes pigment particles. Regardless of the source of the dispersion, in one aspect, additional components can be included in the dispersion, such as surfactants and dispersing agents.

The method can further include forming a mini-emulsion of monomers in an aqueous solution by high energy dispersing methods. Non-limiting examples of such high energy dispersing methods are sonication, micro-fluidization, and high-pressure homogenization. In a specific embodiment, the high energy dispersing method can include sonication.

The monomers used by the present method to encapsulate a pigment particulate can be any monomer presently known in the art. In one embodiment, the monomers can comprise or consist essentially of an acrylate, a methacrylate, or other vinyl-containing monomers such as styrene. Non-limiting examples of monomers include methyl methacrylate, methyl acrylate, ethyl methacrylate, ethyl acrylate, butyl methacrylate, butyl acrylate, hexyl methacrylate, 2-ethylhexyl methacrylate, 2-ethylhexyl acrylate, isobutyl methacrylate, isobutyl acrylate, octyl methacrylate, lauryl methacrylate, dodecyl methacrylate, methacrylic acid, hydroxyl ethyl acrylate, styrene, and mixtures thereof.

In one embodiment, the high energy dispersing methods can be used with the dispersion of pigment particles, and optionally when the pigment particle dispersion and the mini-emulsion are mixed together. In one embodiment, the mini-emulsion can be mixed with the liquid vehicle to produce at least about a 1:1 ratio of monomers to pigment particles by weight. In a further embodiment, the ratio of monomers to pigment particles by weight can be at least about 1.25:1.

The method can further include adding redox initiating agent to the liquid vehicle. A redox initiating agent can include two parts: a reducing agent and an oxidant. In one aspect, the addition of redox initiating agent can take place during or after the mixing of the mini-emulsion with the liquid vehicle. The addition can take place in two or more separate addition steps, by adding, for example, an oxidant and a reducing agent separately. In one embodiment, the reducing agent can be added before the oxidant. An amount of time can be permitted to pass between separate addition steps. For example, less than 30 minutes between addition steps, less than 10 minutes, 5 minutes, or even about 2 minutes can be permitted between addition steps of the redox initiating agent.

As mentioned, the redox initiating agent can include a reducing agent and an oxidant. The reducing agent can be selected from any agent that can function as a reducing agent as is known in the chemical art. Non-limiting examples of reducing agents include ascorbic acid, cupric acetate, cupric benzoylacetonate, ascorbyl palmitate, and combinations thereof. Likewise, the oxidant can be selected from any agent that can function as an oxidizing agent. Non-limiting examples of oxidants include t-butyl hydroperoxide, benzyl peroxide, t-butylperoxymaleic acid, t-butyl perbenzoate, and combinations thereof.

The addition of redox initiating agent to the liquid vehicle can initiate polymerization of the monomers. The pigment particles in the mixture act as nucleating agents and polymerization thus occurs at a surface of the pigment particles. More specifically, the pigments are encapsulated with a polymer that is polymerized at the surface of the pigment in an in situ process. Generally, in one in-situ encapsulation process, a dispersion including monomers and the pigment particles can be homogenized. The monomers in the dispersion are then polymerized at the surface of the pigment so as to encapsulate the pigment particles. Such polymerization at the surface of the pigment particles can partially to fully encapsulate the pigment particle. Therefore, the majority to substantially all of the pigment particles can be at least partially encapsulated by the polymerization process.

The conditions for polymerization can be adjusted according to the materials used to create the encapsulated pigment dispersion. Unlike non-redox-based polymerization, redox-based polymerization can proceed at relatively moderate polymerization conditions and in a relatively fast time. The high reaction temperatures and long reaction times associated with non-redox-based polymerization can destabilize the encapsulated pigment dispersion, particularly at high solids content, and thus limit the total solids content of the dispersion. Therefore, even in dispersions created by other polymerization methods, the high solids content cannot be achieved by subsequent concentrating processes because the encapsulated pigment dispersion is not stable under the concentrated conditions. Conversely, using redox initiating agent to initiate polymerization can produce encapsulated pigment dispersions that are stable at relatively high solids content. Redox-based polymerization can be carried out at temperatures of about 30° C. to about 55° C. In a more detailed embodiment, the polymerization can be carried out at temperatures of about 30° C. to about 50° C. In another embodiment, polymerization can be carried out at room temperature. Additionally, polymerization according to the methods disclosed herein can be completed in a relatively short time. In one embodiment, polymerization can be completed within about 1 hour of adding redox initiating agent. In another embodiment, polymerizing the monomers can be completed within about 30 minutes of adding redox initiating agent.

Pigment particles can be of any form. A particular advantage of the higher solids content of encapsulated pigment dispersions of the present application is the use of the pigment as a component in an ink formulation, wherein the dispersion can be diluted and still produce a useful pigment content in the overall ink formulation. Therefore, in one embodiment, the pigment can be color-imparting pigment. In a specific embodiment, the pigment particles can be selected from yellow pigment, cyan pigment, magenta pigment, black pigment, blue pigment, pink pigment, green pigment, orange pigment, violet pigment, and mixtures thereof. Pigments used in the present methods can comprise or consist essentially of metallic materials. In the cases wherein metallic materials are not present in the pigment, metallic material in the form of particulate can optionally be added to the dispersion of pigment particles or the mixture of pigment particles with the mini-emulsion. Addition of metallic particulate can improve the polymerization process. Specifically, peroxides in a pre-polymerization mixture can undergo reductive activation to yield desired initiating radicals from multivalent metallic compounds, e.g. copper, iron, cobalt, etc. These metallic compounds, particularly in their lowest oxidation state, e.g. $Cu^{+1}$, $Fe^{+2}$, $Co^{+2}$, etc., can act as electron transfer agents for, e.g., peresters and hydroperoxides, and thus can assist in initiating polymerization.

The encapsulated pigment dispersion formed according to the methods herein can have a total solids content of at least 12 wt %. In one embodiment, the encapsulated pigment dispersion can have a total solids content of at least 18 wt %. In still a further embodiment, the encapsulated pigment dispersion can have a total solids content of at least 25 wt %.

The resulting encapsulated pigment dispersion, formed according to the methods outlined herein, can include a plurality of pigment particles substantially encapsulated with polymerized monomers dispersed in substantially all of an aqueous liquid vehicle present during encapsulation. Therefore, the liquid vehicle present during polymerization of the monomers remains as part of the dispersion. The dispersion is not concentrated by removing the liquid vehicle present. On the other hand, the dispersion may be subject to dilution, such as when incorporated into, e.g., an ink. The encapsulated pigment dispersion can have a total solids content of about 18 wt % to about 40 wt %. In a further embodiment, the total solids content of the dispersion can be about 25 wt % to about 40 wt %. In such embodiments, the encapsulated pigment dispersion can be reduced when mixed with the aqueous liquid vehicle by at least 40%. For example, in the case of a dispersion having a total solids content of about 18 wt %, when added in an ink formulation, and reduced by at least 40%, would have a total solids content of at most 10.8 wt % from the encapsulated pigment dispersion. Similarly, a dispersion having a total solids content of about 25 wt %, when reduced by at least 40% would have a resulting solids content of at most 15%. Such resulting solids content values would, obviously, be higher when the total solids content of the initial dispersion is greater than the values noted in the example calculations.

As previously mentioned, the encapsulated pigment dispersion can be included in an ink. In a specific embodiment, a method of forming an ink-jet ink can include mixing an encapsulated pigment dispersion in an aqueous ink vehicle. In one aspect, the ink-jet ink can be substantially free of non-encapsulated pigment.

Typical ink vehicle formulations that can be used with the encapsulated pigment dispersions described herein can include water, and optionally, one or more co-solvents present in total at from about 5 wt % to about 50 wt %. Further, one or more non-ionic, cationic, and/or anionic surfactants can be present. Such surfactants typically range from 0 wt % to 5 wt %. The balance of the formulation can be purified water, or other vehicle components known in the art, such as biocides, viscosity modifiers, materials for pH adjustment, sequestering agents, preservatives, and the like. Typically, the ink vehicle is predominantly water.

Non-limiting examples of classes of co-solvents that can be used can include aliphatic alcohols, aromatic alcohols, diols, glycol ethers, polyglycol ethers, caprolactams, formamides, acetamides, and long chain alcohols. Examples of such compounds include primary aliphatic alcohols, secondary aliphatic alcohols, 1,2-alcohols, 1,3-alcohols, 1,5-alcohols, ethylene glycol alkyl ethers, propylene glycol alkyl ethers, higher homologs of polyethylene glycol alkyl ethers, N-alkyl caprolactams, unsubstituted caprolactams, both substituted and unsubstituted formamides, both substituted and unsubstituted acetamides, and the like. Specific examples of solvents that can be used include trimethylolpropane, 2-pyrrolidinone, and 1,5-pentanediol.

One or more of many surfactants can also be used as are known by those skilled in the art of ink formulation and may be alkyl polyethylene oxides, alkyl phenyl polyethylene oxides, polyethylene oxide block copolymers, acetylenic polyethylene oxides, polyethylene oxide (di)esters, polyethylene oxide amines, protonated polyethylene oxide amines, protonated polyethylene oxide amides, dimethicone copolyols, substituted amine oxides, and the like. Typically, surfactant can be added in the range from 0 wt % to 5 wt %.

Consistent with the methods of this invention, various other additives may be employed to optimize the properties of the ink composition for specific applications. Examples of these additives are those added to inhibit the growth of harmful microorganisms. These additives may be biocides, fungicides, and other microbial agents, which are routinely used in ink formulations. Examples of suitable microbial agents include, but are not limited to, Nuosept (Nudex, Inc.), Ucarcide (Union carbide Corp.), Vancide (R.T. Vanderbilt Co.), Proxel (ICI America), and combinations thereof.

Sequestering agents, such as EDTA (ethylene diamine tetra acetic acid), may be included to eliminate the deleterious effects of heavy metal impurities, and buffer solutions may be used to control the pH of the ink. From 0 wt % to 2 wt %, for example, can be used. Viscosity modifiers and buffers may also be present, as well as other additives known to those skilled in the art to modify properties of the ink as desired. Such additives can be present at from 0 wt % to 20 wt %.

The ink-jet inks made according to the methods herein can generally provide several advantages. For example, the use of polymer encapsulated pigments tends to reduce the number of total particles in solution (as opposed to having separate latex particulates co-dispersed with the pigments) and their combined surface areas such that the pigment suspension, e.g., ink, viscosity can be reduced. Encapsulation also prevents pigment-latex separation when applied to a substrate, e.g., ink printed on a media substrate, such that durability and optical density are more optimized. Polymer-encapsulated pigments also facilitate the result that each pigment particle becomes trapped below the surface of latex formed films (after printing) such that gloss and color-to-color gloss uniformity is enhanced.

Encapsulated pigment dispersions according to the present invention can have high solids content, which can allow for broad incorporation into ink formulations. Further, the methods taught herein can be carried out at lower temperatures than other encapsulation methods, and in shorter time, both of which improve process efficiency and can reduce production cost. Also, the encapsulated pigment dispersions having high solids content are inherently more stable because of the mild to moderate processing conditions.

EXAMPLES

The following examples illustrate embodiments of the invention that are presently known. Thus, these examples should not be considered as limitations of the present invention, but are merely in place to teach how to make the best-known compositions of the present invention based upon current experimental data. As such, a representative number of compositions and their method of manufacture are disclosed herein.

Example 1

Preparation of Encapsulated Yellow Pigment Dispersion

A first mixture containing 125 g of Pigment Yellow 213 (containing 20 wt % pigment) was sonicated at full power for 2 minutes. A second mixture was prepared using 18.0 g methyl methacrylate, 6.0 g butyl acrylate, 0.2 g methacrylic acid, 0.5 g hydroxyl ethyl acrylate, 0.5 g hexadecane, 8.0 g of 10% aqueous sodium dodecyl sulfate (SDS) solution, and 41.8 g water. The second mixture was separately sonicated for 2 minutes. The first mixture and the second mixture were mixed together to create a third mixture. The third mixture was sonicated for 2 more minutes. Following sonication, the mixture was charged into a 500 ml reactor equipped with an agitator and a condenser. To the mixture was added 0.95 g of dioctyl sodium sulfosuccinate (Aerosol OT). The reactor was heated to 50° C., at which point, 0.2 g of ascorbic acid in 10.0 g of water was added. Five minutes later, 0.2 g of t-butyl hydroperoxide was added. The mixture was held at 50° C. for 30 minutes from the time of t-butyl hydroperoxide addition. The reaction mixture was cooled and filtered through a one-micro sized filter. The total solid content was 24.8 wt %.

Example 2

Preparation of Encapsulated Cyan Pigment Dispersion

A first mixture containing 125 g of Cyan PB 15:3 dispersion (containing 18 wt % pigment) was sonicated at full power for 2 minutes. A second mixture was prepared using 18.0 g methyl methacrylate, 6.0 g butyl acrylate, 0.2 g methacrylic acid, 0.5 g hydroxyl ethyl acrylate, 0.5 g hexadecane, 8.0 g of 10% aqueous sodium dodecyl sulfate (SDS) solution, and 41.8 g water. The second mixture was separately sonicated for 2 minutes. The first mixture and the second mixture were mixed together to create a third mixture. The third mixture was sonicated for 2 more minutes. Following sonication, the mixture was charged into a 500 ml reactor equipped with an agitator and a condenser. To the mixture was added 0.95 g of dioctyl sodium sulfosuccinate (Aerosol OT). The reactor was heated to 50° C., at which point, 0.2 g of ascorbic acid in 10.0 g of water was added. Five minutes later, 0.2 g of t-butyl hydroperoxide was added. The mixture was held at 50° C. for 30 minutes from the time of t-butyl hydroperoxide addition. The reaction mixture was cooled and filtered through a one-micro sized filter. The total solid content was 21.2 wt %.

Example 3

Preparation of Encapsulated Yellow Pigment Dispersion II

A first mixture containing 100 g of Pigment Yellow 213 (containing 20 wt % pigment) was sonicated at full power for 2 minutes. A second mixture was prepared using 14.75 g methyl methacrylate, 4.75 g butyl acrylate, 0.2 g methacrylic acid, 0.5 g hydroxyl ethyl acrylate, 0.5 g hexadecane, 8.0 g of 10% aqueous sodium dodecyl sulfate (SDS) solution, and 71.3 g water. The second mixture was separately sonicated for 2 minutes. The first mixture and the second mixture were mixed together to create a third mixture. The third mixture was sonicated for 2 more minutes. Following sonication, the mixture was charged into a 500 ml reactor equipped with an agitator and a condenser. To the mixture was added 0.95 g of dioctyl sodium sulfosuccinate (Aerosol OT). The reactor was heated to 50° C., at which point, 0.2 g of ascorbic acid in 10.0 g of water was added. Five minutes later, 0.2 g of t-butyl hydroperoxide was added. The mixture was held at 50° C. for 30 minutes from the time of t-butyl hydroperoxide addition. The reaction mixture was cooled and filtered through a one-micro sized filter. The total solid content was 19.9 wt %.

Example 4

Preparation of Encapsulated Cyan Pigment Dispersion II

A first mixture containing 100 g of Cyan PB 15:3 dispersion (containing 18 wt % pigment) was sonicated at full power for 2 minutes. A second mixture was prepared using 14.75 g methyl methacrylate, 4.75 g butyl acrylate, 0.2 g methacrylic acid, 0.5 g hydroxyl ethyl acrylate, 0.5 g hexadecane, 8.0 g of 10% aqueous sodium dodecyl sulfate (SDS) solution, and 71.3 g water. The second mixture was separately sonicated for 2 minutes. The first mixture and the second mixture were mixed together to create a third mixture. The third mixture was sonicated for 2 more minutes. Following sonication, the mixture was charged into a 500 ml reactor equipped with an agitator and a condenser. To the mixture was added 0.95 g of dioctyl sodium sulfosuccinate (Aerosol OT). The reactor was heated to 50° C., at which point, 0.2 g of ascorbic acid in 10.0 g of water was added. Five minutes later, 0.2 g of t-butyl hydroperoxide was added. The mixture was held at 50° C. for 30 minutes from the time of t-butyl hydroperoxide addition. The reaction mixture was cooled and filtered through a one-micro sized filter. The total solid content was 16.5 wt %.

Example 5

Preparation of Encapsulated Yellow Pigment Dispersion III

A first mixture containing 90 g of Pigment Yellow 213 (containing 20 wt % pigment, and having synergist dispersing agent) and 10 g of water was sonicated at full power for 2 minutes. A second mixture was prepared using 13.25 g methyl methacrylate, 4.25 g butyl acrylate, 0.2 g methacrylic acid, 0.5 g hydroxyl ethyl acrylate, 0.5 g hexadecane, 8.0 g of 10% aqueous sodium dodecyl sulfate (SDS) solution, and 73.3 g water. The second mixture was separately sonicated for 2 minutes. The first mixture and the second mixture were mixed together to create a third mixture. The third mixture was sonicated for 2 more minutes. Following sonication, the mixture was charged into a 500 ml reactor equipped with an agitator and a condenser. To the mixture was added 0.95 g of dioctyl sodium sulfosuccinate (Aerosol OT). The reactor was heated to 50° C., at which point, 0.2 g of ascorbic acid in 10.0 g of water was added. Five minutes later, 0.2 g of t-butyl hydroperoxide was added. The mixture was held at 50° C. for 30 minutes from the time of t-butyl hydroperoxide addition. The reaction mixture was cooled and filtered through a one-micro sized filter. The total solid content was 18.2 wt %.

Example 6

Preparation of Encapsulated Yellow Pigment Dispersion IV

A first mixture containing 90 g of Pigment Yellow 213 (containing 20 wt % pigment, and having non-synergist dispersing agent) and 10 g of water was sonicated at full power for 2 minutes. A second mixture was prepared using 13.25 g methyl methacrylate, 4.25 g butyl acrylate, 0.2 g methacrylic acid, 0.5 g hydroxyl ethyl acrylate, 0.5 g hexadecane, 8.0 g of 10% aqueous sodium dodecyl sulfate (SDS) solution, and 73.3 g water. The second mixture was separately sonicated for 2 minutes. The first mixture and the second mixture were mixed together to create a third mixture. The third mixture was sonicated for 2 more minutes. Following sonication, the mixture was charged into a 500 ml reactor equipped with an agitator and a condenser. To the mixture was added 0.95 g of dioctyl sodium sulfosuccinate (Aerosol OT). The reactor was heated to 50° C., at which point, 0.2 g of ascorbic acid in 10.0 g of water was added. Five minutes later, 0.2 g of t-butyl hydroperoxide was added. The mixture was held at 50° C. for 30 minutes from the time of t-butyl hydroperoxide addition. The reaction mixture was cooled and filtered through a one-micro sized filter. The total solid content was 17.0 wt %.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

What is claimed is:

1. A method of forming an encapsulated pigment dispersion, comprising:
    forming a pigment dispersion by dispersing pigment particles in a liquid vehicle;
    forming a mini-emulsion of monomers in an aqueous solution by a high energy dispersing method;
    mixing the mini-emulsion with the pigment dispersion to produce a prepolymer mixture;
    adding a redox initiating agent to the prepolymer mixture; and
    polymerizing the monomers on a surface of the pigment particles at a temperature of about 30° C. to about 55° C. to form the encapsulated pigment dispersion having a total encapsulated pigment solids content of at least 25 wt %.

2. A method as in claim 1, wherein the prepolymer mixture has at least about a 1:1 ratio of monomers to pigment particles by weight.

3. A method as in claim 1, wherein the high energy dispersing method includes sonication.

4. A method as in claim 1, wherein the step of adding the redox initiating agent includes at least two separate additions.

5. A method as in claim 1, wherein the redox initiating agent includes an oxidant selected from t-butyl hydroperoxide, benzyl peroxide, t-butylperoxymaleic acid, t-butyl perbenzoate, and mixtures thereof.

6. A method as in claim 1, wherein the redox initiating agent includes a reducing agent selected from ascorbic acid, cupric acetate, cupric benzoylacetonate, ascorbyl palmitate, and mixtures thereof.

7. A method as in claim 1, wherein the pigment particles are selected from yellow pigment, cyan pigment, magenta pigment, black pigment, blue pigment, pink pigment, green pigment, orange pigment, violet pigment, and mixtures thereof.

8. A method as in claim 1, wherein the step of polymerizing the monomers is completed within about 1 hour of adding redox initiating agent.

9. A method as in claim 1, wherein the step of polymerizing the monomers is completed within about 30 minutes of adding redox initiating agent.

10. A method as in claim 1, wherein the encapsulated pigment dispersion is substantially free of non-encapsulated pigment.

11. A method of forming an ink-jet ink, comprising:
    mixing an encapsulated pigment dispersion in an aqueous ink vehicle, said encapsulated pigment dispersion prepared by:
    forming a pigment dispersion by dispersing pigment particles in a liquid vehicle;
    forming a mini-emulsion of monomers in an aqueous solution by a high energy dispersing method;
    mixing the mini-emulsion with the pigment dispersion to produce prepolymer mixture;
    adding a redox initiating agent to the prepolymer mixture; and
    polymerizing the monomers on a surface of the pigment particles at a temperature of about 30° C. to about 55° C. to form the encapsulated pigment dispersion having a total encapsulated pigment solids content of at least 25 wt %, which is reduced when mixed with the aqueous liquid vehicle by at least 40%.

12. A method as in claim 11, wherein the pigment includes yellow pigment, cyan pigment, magenta pigment, black pigment, blue pigment, pink pigment, green pigment, orange pigment, violet pigment, and mixtures thereof.

13. A method as in claim 11, wherein the ink-jet ink is substantially free of non-encapsulated pigment.

14. A method as in claim 11, wherein the prepolymer mixture has at least about a 1:1 ratio of monomers to pigment particles by weight.

15. An encapsulated pigment dispersion, comprising:
    a liquid vehicle; and
    a plurality of polymer encapsulated pigment particles dispersed in the liquid vehicle, wherein the encapsulated pigment dispersion has a total encapsulated pigment solids content of about 25 wt % to about 40 wt % and wherein the plurality of polymer encapsulated pigment particles has a polymer capsule to pigment weight ratio of at least about 1:1.

16. A dispersion as in claim 15, wherein the liquid vehicle is substantially devoid of non-encapsulated pigment.

* * * * *

UNITED STATES PATENT AND TRADEMARK OFFICE
CERTIFICATE OF CORRECTION

PATENT NO. : 8,383,701 B2
APPLICATION NO. : 11/800351
DATED : February 26, 2013
INVENTOR(S) : Hui Liu Page 1 of 1

It is certified that error appears in the above-identified patent and that said Letters Patent is hereby corrected as shown below:

In the Claims

In column 10, line 41, in Claim 11, delete "40%" and insert -- 40 wt % --, therefor.

Signed and Sealed this
Sixteenth Day of July, 2013

Teresa Stanek Rea
*Acting Director of the United States Patent and Trademark Office*